United States Patent [19]

Kormann et al.

[11] Patent Number: 5,769,937
[45] Date of Patent: Jun. 23, 1998

[54] HIGH-PURITY FERROMAGNETIC IRON OXIDE PIGMENTS

[75] Inventors: Claudius Kormann, Bingen; Ekkehard Schwab, Neustadt; Reinhold Schlegel, Hassloch, all of Germany

[73] Assignee: BASF Aktiengesellschaft, Ludwigshafen, Germany

[21] Appl. No.: 793,071

[22] PCT Filed: Aug. 16, 1995

[86] PCT No.: PCT/EP95/03230

§ 371 Date: Feb. 18, 1997

§ 102(e) Date: Feb. 18, 1997

[87] PCT Pub. No.: WO96/06891

PCT Pub. Date: Mar. 7, 1996

[30]  Foreign Application Priority Data

Aug. 26, 1994 [DE]  Germany ............... 44 30 285.1

[51] Int. Cl.⁶ ............... C09C 1/24; C09D 17/00; C01G 49/06; C01G 49/08
[52] U.S. Cl. ............... 106/456; 423/634; 423/632; 252/62.56
[58] Field of Search ............... 106/456; 423/634, 423/632; 252/62.56

[56]  References Cited

U.S. PATENT DOCUMENTS 4,631,089  12/1986  Rademachers et al. ............... 106/456

FOREIGN PATENT DOCUMENTS 57-200230  12/1982  Japan .

OTHER PUBLICATIONS

Ullmann's Encyclopedia of Industrial Chemistry, vol. A14, 5th Ed. pp. 595–601, 1989 no month.

*Primary Examiner*—Melissa Bonner
*Attorney, Agent, or Firm*—Keil & Weinkauf

[57]  ABSTRACT $\gamma$-$Fe_2O_3$ pigments and $Fe_3O_4$ pigments with a particle diameter of 2 to 100 nm, a saturation magnetization above 40 $nTm^3/g$, a remanence below 10 $nTm^3/g$, a Cr content below 40 mg/kg of pigment, a Cu content below 40 mg/kg of pigment and C content below 100 mg/kg of pigment and aqueous suspension of these pigments. The pigments are used in aqueous suspension in the medical sector, in particular as contrast agents in magnetic resonance imaging.

4 Claims, No Drawings

HIGH-PURITY FERROMAGNETIC IRON OXIDE PIGMENTS

The present invention relates to high-purity $\gamma$-$Fe_2O_3$ pigments and $Fe_3O_4$ pigments with a particle diameter of 2-100 nm, a saturation magnetization above 40 $nTm^3/g$, a remanence below 10 $nTm^3/g$, a Cr content below 40 mg/kg of pigment, a Cu content below 40 mg/kg of pigment and a C content below 100 mg/kg of pigment.

The invention additionally relates to processes for preparing these pigments, to aqueous suspensions which contain these pigments, and to the use of the pigments and suspensions in the medical sector.

Ferromagnetic iron oxide pigments are known to be usable in the medical sector in particular in the form of an aqueous suspension, as contrast agents in magnetic resonance imaging.

The pigments are known to be prepared by reacting an aqueous solution of iron salts with a base, adjusting the iron valency required in the pigment by using iron(II) and iron(III) salts or, if the iron valency is too low, by oxidative treatment of the solution, eg. with atmospheric oxygen. The precipitate is then separated off and washed and dried in a conventional way.

The iron salts used as starting compounds still contain, however, small amounts of salts of other metals such as chromium, nickel and copper. These impurities do not interfere with use for most purposes but are not physiologically acceptable if, like contrast agents, they are put directly into the bloodstream in the human body.

Furthermore, iron pigments suitable for magnetic resonance imaging must meet high demands in respect of ferromagnetic sensitivity, for which the level of the saturation magnetization at low remanence represents a measure, in order thereby to keep the dose of the agent as small as possible. Finally, these contrast agents should have particles as fine as possible so that they will dissolve faster in the blood and do not form any deposits which are difficult to break down on the blood vessel walls.

Contrast agents with these properties have not previously been available, and accordingly it is an object of the present invention to remedy this deficiency.

It is an object of the present invention therefore to prepare, in an industrially simple and economic manner, ferromagnetic iron oxide pigments which are suitable for medical purposes, in particular as contrast agents for magnetic resonance imaging, and which have a distinctly reduced content of impurities.

We have found that this object is achieved by $\gamma$-$Fe_2O_3$ pigments and $Fe_3O_4$ pigments with an average particle diameter of 2-100 nm, a saturation magnetization above 40 $nTm^3/g$, a remanence below 10 $nTm^3/g$, a Cr content below 40 mg/kg of pigment, a Cu content below 40 mg/kg of pigment and a C content below 100 mg/kg of pigment.

We have additionally found a process for preparing these pigments, and the use of these pigments as contrast agents in magnetic resonance imaging.

It is necessary to employ the iron or an iron oxide in highly pure form as precursor for preparing pigments of this type. Precursors of this type can be obtained from iron compounds obtainable by simple chemical or physical purification, preferably distillation. Particularly suitable for this purpose are volatile iron compounds, in particular iron carbonyls such as iron pentacarbonyl.

Iron pentacarbonyl can be prepared and purified by distillation in a conventional way, as described, for example, in Ullmann's Encyclopedia of Industrial Chemistry, 5th edition, volume A14, pages 595–601, VCH Verlagsgesellschaft mbH, 1989.

Iron can be obtained in a conventional way from iron pentacarbonyl by thermal decomposition at 60°–300° C., preferably 150°–250° C. Suitable for preparing iron oxides from iron carbonyls are normally oxidative decomposition of iron pentacarbonyl with oxygen or an oxygen-containing gas.

Iron oxides of these types, some of which are commercially available, have a considerable content of non-ferromagnetic iron oxides such as $\alpha$-$Fe_2O_3$ with a large particle size which is unwanted for use as contrast agents in magnetic resonance imaging, and must therefore converted into fine-particle, ferromagnetic iron oxides such as $\gamma$-$Fe_2O_3$ or $Fe_3O_4$.

$\gamma$-$Fe_2O_3$ particles of this type can be prepared by dissolving the iron or, advantageously, an iron oxide, in particular an oxide of trivalent iron, in a high-purity aqueous mineral acid, preferably hydrochloric acid. When iron is used, or when the iron oxide is not in trivalent form or is only partially in trivalent form, oxidizing conditions are preferably used, in particular in the presence of oxygen or an oxygen-containing gas. The ferromagnetic pigment is then precipitated by adding the solution gradually to a mineral base, preferably sodium hydroxide solution. To obtain particles of the desired fineness, the precipitation is carried out with vigorous stirring, the energy preferably being 0.05–5 kWh per kg of the precipitation mixture. It is advisable to carry out the precipitation at from 5° to 40° C., preferably 10° to 30° C.

After the precipitation, the precipitate is separated off by decantation, filtration or centrifugation and washed until ions are no longer detectable in the eluate. The pigment can then be dried or converted directly into an aqueous suspension ready for use.

To prepare $Fe_3O_4$ it is suitable to dissolve iron or an iron oxide in a high-purity aqueous mineral acid, preferably hydrochloric acid. The molar ratio of trivalent to divalent iron should be adjusted to 2:1 or approximately 2:1 if the iron oxide used does not (approximately) have this ratio. If the average valency of the iron is too low, this can take place by oxidation, preferably with oxygen or an oxygen-containing gas, and if the average valency of the iron is too high it can take place by reduction or, advantageously, by adding an iron(II) salt solution obtainable, for example, by dissolving pure iron in a high-purity aqueous mineral acid under non-oxidizing conditions, such as under a protective gas. Further reaction with a mineral base should advantageously be carried out as described above.

The pigments according to the invention are primarily used for preparing aqueous suspensions which in turn are particularly used as contrast agents for magnetic resonance imaging. The pigment concentration in the suspensions is preferably 0.0001 to 0.6, in particular 0.001 to 0.3, % by weight. As medical products, these suspensions can contain auxiliaries in conventional amounts, eg. physiologically acceptable protective colloids or dispersants such as polyacrylates or proteins, and buffer substances to adjust a pH which is preferably from 6 to 12, in particular from 6.5 to 8. Otherwise, the suspensions are used for magnetic resonance imaging in the same way as conventional products of this type.

EXAMPLE 7.8 kg of high-purity 38% by weight hydrochloric acid were added to a suspension of 2 kg of high-purity $\alpha$-$Fe_2O_3$ in 10 kg of distilled water, and the mixture was heated until the iron oxide had dissolved.

After this solution had cooled to room temperature it was mixed with 4.7 kg of a 33% by weight iron(II) chloride solution which had been prepared by dissolving extra pure iron in high-purity hydrochloric acid.

The resulting solution was then gradually added under nitrogen with vigorous stirring (0.9 kWh stirring energy) to 17.5 kg of a 25% by weight NaOH solution at 20° C. over the course of 13.5 h.

The precipitate was filtered off, washed and dried.

It contained as impurities 24 mg of chromium, <30 mg of copper and 80 mg of carbon per kg of pigment and had an average particle diameter of 15 nm. The saturation magnetization was 74 $nTm^3/g$ and the remanence was 5 $nTm^3/g$.

We Claim:

1. A process for preparing ferromagnetic iron oxide pigments having an average particle diameter of 2–100 nm, a saturation magnetization above 40 $nTm^3/g$, a remanence below 10 $nTm^3/g$, which comprises dissolving iron or an iron oxide which contains below 40 ppm Cr, below 40 ppm Cu and below 100 ppm C in a high-purity aqueous mineral acid, and precipitating $\gamma$-$Fe_2O_3$ from this solution at 5°–40° C. with vigorous stirring using a mineral base, operating under oxidizing conditions in the case of iron or if the iron oxide employed is not present in trivalent form or is only partially present in trivalent form, and washing and drying the fine-particle precipitate obtained in this way.

2. The process of claim 1, wherein $\gamma$-$Fe_2O_3$ pigments are prepared.

3. A process for preparing ferromagnetic iron oxide pigments pas claimed in claim 1, having a saturation magnetization above 40 $nTm^3/g$ and a remanence below 10 $nTm^3/g$, which comprises dissolving iron or an iron oxide which contains below 40 ppm Cr, below 40 ppm Cu and below 100 ppm C in a high-purity aqueous mineral acid, adjusting a molar ratio of trivalent to divalent iron of 2:1 or approximately 2:1 if the solution does not have this ratio or approximately this ratio, and precipitating $Fe_3O_4$ from this solution at 5°–40° C. with vigorous stirring using a mineral base, and washing and drying the fine-particle precipitate obtained in this way.

4. The process of claim 3, wherein $Fe_3O_4$ pigments are prepared.

* * * * *

UNITED STATES PATENT AND TRADEMARK OFFICE
CERTIFICATE OF CORRECTION

PATENT NO.: 5,769,937

DATED: June 23, 1998

INVENTOR(S): KORMANN et al.

It is certified that error appears in the above-identified patent and that said Letters Patent is hereby corrected as shown below:

Column 4, claim 3, line 2, delete "pas claimed in claim 1,".

Signed and Sealed this

Fifth Day of January, 1999

Attest:

Attesting Officer

*Acting Commissioner of Patents and Trademarks*